United States Patent [19]

Uhing et al.

[11] 4,130,583

[45] Dec. 19, 1978

[54] PROCESS FOR PREPARING ALKYL- OR ARYLPHOSPHONOTHIOIC DIHALIDES

[75] Inventors: Eugene H. Uhing, Ridgewood, N.J.; Arthur D. F. Toy, Stamford, Conn.

[73] Assignee: Stauffer Chemical Company, Westport, Conn.

[21] Appl. No.: 769,474

[22] Filed: Feb. 17, 1977

Related U.S. Application Data

[63] Continuation of Ser. No. 551,805, Feb. 20, 1975, abandoned.

[51] Int. Cl.$^2$ ............................ C07F 9/34; C07F 9/04
[52] U.S. Cl. ................................................. 260/543 P
[58] Field of Search ...................................... 260/543 P

[56] References Cited

U.S. PATENT DOCUMENTS

| | | | |
|---|---|---|---|
| 3,457,305 | 7/1969 | Baker et al. | 260/543 P |
| 3,457,307 | 7/1969 | Groenweghe et al. | 260/543 P |

FOREIGN PATENT DOCUMENTS

| | | | |
|---|---|---|---|
| 300472 | 4/1971 | U.S.S.R. | 260/543 P |

*Primary Examiner*—Norman Morgenstern
*Attorney, Agent, or Firm*—William R. Robinson

[57] ABSTRACT

Alkyl- or arylphosphonothioic dihalides are prepared by contacting a dialkyl or diaryl thioether with various phosphorus containing reactants including: $PCl_3$, $PBr_3$, $P(S)Cl_3$, $P(S)Br_3$, $P_4S_3$, $P_4S_5$, $P_4S_7$, $P_4S_{10}$ and elemental phosphorus under at least autogenous pressure at a temperature of from about 200° C. to about 400° C. The compounds obtained are useful as constituents in insecticides, fungicides, pharmaceuticals, and as intermediates in preparation of other organophosphorus compounds.

6 Claims, No Drawings

PROCESS FOR PREPARING ALKYL- OR ARYLPHOSPHONOTHIOIC DIHALIDES

This is a continuation, of application Ser. No. 551,805 filed Feb. 20, 1975 now abandoned.

BACKGROUND OF THE INVENTION

1. Field of the Invention

The present invention relates to new and improved processes for the preparation of alkyl- or arylphosphonothioic dihalides.

2. The Prior Art

Alkylphosphonothioic dihalides have been prepared in the prior art by reacting alkyl halides with phosphorus trihalides in the presence of aluminum chloride. The reaction proceeds at room temperature according to the formula set forth in Heuben-Weyl, *Methoden der Organis Chenchemie*, Volume 12, part 1 (1965) at page 396.

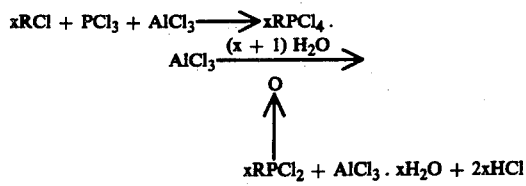

The Heuben-Weyl reference also notes that the reaction has been attempted in the absence of the aluminum chloride catalyst with little success. The alkylphosphonothioic dihalides are prepared by replacing the oxygen of the alkylphosphonic dihalide with sulfur as shown on page 553 of the Heuben-Weyl reference. The yields of the replacement reaction are limited to the yields obtained in the initial reaction forming the alkylphosphonic dihalide.

Other methods of preparing alkylphosphonothioic dihalides are described in *Journal of the American Chemical Society* 88 p. 3041 (1966).

Alkylphosphonothioic dihalides also can be prepared according to our U.S. Pat. No. 3,790,629 by reacting an aliphatic hydrocarbon with a pentavalent thiophosphorus compound having at least two halogens attached thereto under at least autogenous pressure at a temperature of from 200° C. to 450° C.

Cycloalkanephosphonothioic dichlorides have been prepared by reacting a cycloalkene with thiophosphoryl chloride under irradiation with mercury lamps. Reaction times are long and low yields are reported (Angew, Chem. Internat, Edit., vol. 9 (1970), No. 6 at p. 458).

SUMMARY OF THE INVENTION

In accordance with the present invention, there are provided new processes for preparing compounds of the formula:

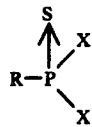
(I)

wherein R is a hydrocarbyl group consisting of hydrogen and carbon including $C_1$ to $C_{20}$ alkyl and the aryl (1 and 2 fused rings) substituted derivatives thereof, cycloalkyl of 5-6 carbons in the ring, aryl of up to 3 fused rings or biphenyl and the $C_1$-$C_4$ alkyl substituted derivatives of said cycloalkyl, aryl, or biphenyl and X is chlorine or bromine.

Typical alkyl groups include methyl, ethyl, n-propyl and isopropyl, n-butyl, isobutyl, tert-butyl, pentyl, hexyl, heptyl, octyl, nonyl, decyl, dodecyl, tetradecyl, hexadecyl, octadecyl and eicosyl. Some suitable aralkyl groups are phenylmethyl, phenylethyl, phenylbutyl, phenyloctyl, phenylhexadecyl, and the corresponding naphthyl derivatives. Ring systems wherein R is cycloalkyl having 5-6 carbons in the ring are illustrated by cyclopentyl and cyclohexyl and its derivatives.

Examples of aryl and substituted aryl groups include phenyl, methylphenyl, ethylphenyl, propylphenyl, and butylphenyl, naphthyl, methylnaphthyl, ethylnaphthyl, propylnaphthyl, butylnaphthyl, anthryl, methylanthryl, propylanthryl, butylanthryl, as well as dimethylphenyl, dimethylnaphthyl, diethylanthryl, and the like. Any of said groups can contain one or more alkyl radicals and any isomeric form of said groups can be used.

Biphenyl R groups include the $C_1$ to $C_4$ alkyl substituted derivatives such as methylbiphenyl and ditolyl. There can be one or more substituents as desired and said substituents can be in any isomeric position desired. The R groups also can be connected to the phosphorus at any isomeric position.

With respect to X, chlorine is preferred over bromine as it is inexpensive and reacts readily. Bromine, however, can be used if it is desired to have bromine in the final compound. Also, bromine is useful in the preparation of bromine containing intermediates for flame retardant compounds.

The process of the present invention comprises contacting a dialkyl or diaryl thioether reactant of the formula:

$$R_2S \qquad (II)$$

wherein R is as defined above, with various phosphorus containing reactants including $PX_3$, $P(S)X_3$, $P_4S_3$, $P_4S_5$, $P_4S_7$, $P_4S_{10}$ and elemental phosphorus, where X is as defined above.

Any combination of the above-identified phosphorus sulfides and, optionally, phosphorus can be used in appropriate quantities to give the P:S ratio desired for a reaction.

Representative dialkyl and diaryl thioethers within the formula (II) include dimethyl, dipropyl, dibutyl, dioctyl, didecyl, didoecyl, dihexadecyl, dioctadecyl, dieicosyl, dicyclopentyl, dicyclohexyl, dibenzyl, ditolyl, diethylbenzyl, dipropylbenzyl, dibutylbenzyl, dinaphthyl, dimethylnaphthyl, dibutylnaphthyl, dianthryl, dimethylanthryl, and dibutylanthryl thioethers, and the like.

The foregoing compounds are given as illustrative and are in no way considered to be totally inclusive of all of the dialkyl and diaryl thioethers which can be used in the method of the present invention. Dialkyl and diaryl thioethers are known and can be obtained commercially or prepared by conventional methods.

In the trivalent phosphorus halide ($PX_3$) reactants and the pentavalent thiophosphoryl halide ($P(S)X_3$) reactants, the three halogens preferably are the same halogen although mixed halogens can be used. The chlorine derivatives is preferred for the reasons previously set forth in this specification. The bromine species, however, can be utilized if desired. These reactants are known and can be obtained commercially or be prepared by conventional methods.

The phosphorus sulfides, $P_4S_3$, $P_4S_5$, $P_4S_7$, and $P_4S_{10}$ are known. Of these, $P_4S_3$ and $P_4S_{10}$ can be easily obtained commercially and therefore are preferred for economic reasons. However, phosphorus sulfides having a specific phosphorus to sulfur ratio can be prepared by reacting the appropriate quantity of Various types of elemental phosphorus can be used including yellow phosphorus and white phosphorus.

The following general elemental equation (2) is representative of reactions according to the present invention:

$$R_2S + 2P + S + 2X_2 \rightarrow 2RP(S)X_2 \quad (2)$$

where R and X are as defined above.

Some illustrative equations according to equation (2) are as follows:

$$6R_2S + 8PX_3 + 3/5\ P_4S_{10} + 8/5\ P \rightarrow 12RP(S)X_2 \quad (3)$$

$$6R_2S + 8PX_3 + 3/4\ P_4S_7 + 1/4\ P_4S_3 \rightarrow 12RP(S)X_2 \quad (4)$$

$$6R_2S + 2PX_3 + 6P(S)X_3 + 4P \rightarrow 12RP(S)X_2 \quad (5)$$

$$6R_2S + 8PX_3 + 3/7\ P_4S_{10} + 4/7\ P_4S_3 \rightarrow 12RP(S)X_2 \quad (6)$$

where R and X are as defined above.

Reactants utilized in the process of the present invention can be employed in stoichiometric amounts, although a sight excess of any of the reactants can be used if desired.

The mechanism of the reaction is not completely understood. The reaction schemes are postulated only and applicants do not intend to limit their process thereto.

It is also to be understood that the process of the present invention can proceed either with the trivalent phosphorus halide or the thiophosphoryl halide alone or mixtures thereof.

The processes of the present invention are carried out at elevated temperatures and at least at autogenous pressures. Temperatures of from about 200° C. to about 400° C. and preferably from about 250° C. to about 375° C. are generally employed. The pressures can be from about 1 to about 300 atmospheres although pressures from about 10 to about 100 atmospheres are generally utilized.

Reaction times can vary over relatively wide ranges and can easily be determined by one skilled in the art. Factors affecting reaction time include reactivity of the reactants and temperature. For example, reactivity of dialkyl thioethers increases with chain length and reaction time therefore decreases accordingly. Reaction time generally decreases with increases in reaction temperature. Typical reaction times are from about 1 to about 24 hours, but greater or lesser reaction times can be employed.

The processes of the present invention can conveniently be effected by introducing the individual reactants into a reaction zone capable of withstanding elevated pressure, such as a metal bomb, autoclave, or other pressure vessel, and carrying out the reaction under at least the autogenous pressure developed by the reactants at the reaction temperature. An agitation means should be provided for said reaction zone. The reaction can be carried out in a continuous or batchwise system as desired.

The products of the reaction are purified by conventional methods such as by fractional distillation of liquids and sublimation, crystallization or extraction of solid products.

The identification of products is achieved by conventional methods, such as elemental analysis, and gas chromatography for purity and mass spectrometer and nuclear magnetic resonance and infrared analysis to establish structure.

Illustrative of the compounds which can be prepared by the processes of the present invention are: Alkyl:

$CH_3P(S)Cl_2$
$CH_3P(S)Br_2$
$C_2H_5P(S)Cl_2$
$C_2H_5P(S)Br_2$
$C_3H_7P(S)Cl_2$
$C_4H_9P(S)Cl_2$
$C_4H_9P(S)Br_2$
$C_5H_{11}P(S)Cl_2$
$C_8H_{17}P(S)Cl_2$
$C_8H_{17}P(S)Br_2$
$C_{18}H_{37}P(S)Cl_2$
$(CH)_3CCH_2P(S)Cl_2$

CYCLIC COMPOUNDS
Aromatic Series

Benzene:

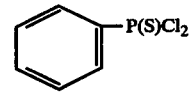

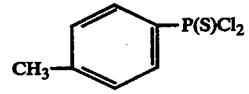

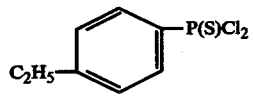

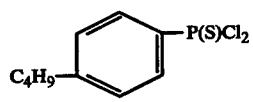

Napthalene:

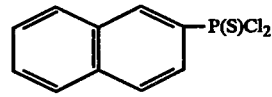

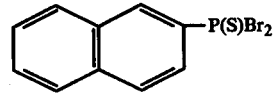

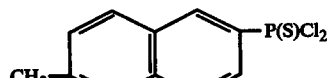

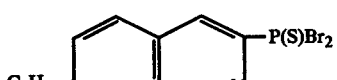

Anthracene:

-continued

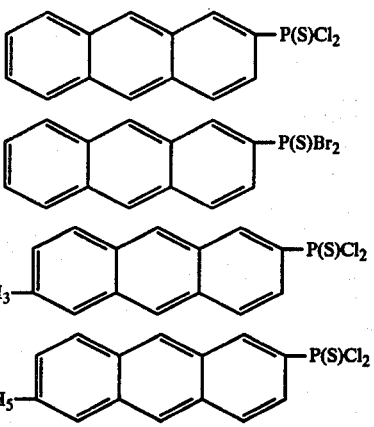

Biphenyl:

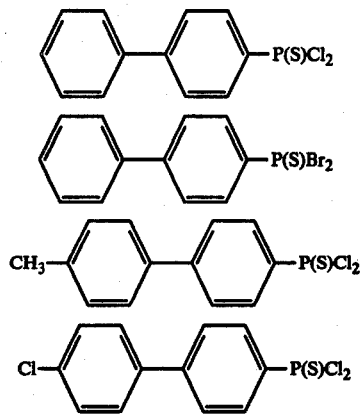

Cycloalkyl:
5-membered Carbon Ring:

6-membered carbon ring:

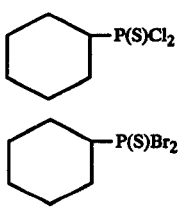

The products of the present invention are dihalides of pentavalent phosphorus and, therefore, can be subject to all the known reactions which such compounds undergo. Said products can be used to make insecticides as illustrated by the process for making O-ethyl O-paranitrophenyl phenylphosphonothioate as per the following illustrative reaction scheme:

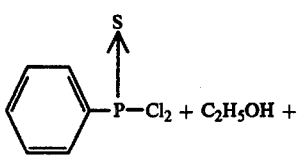

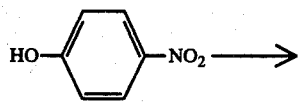

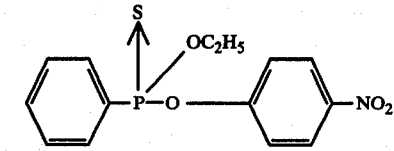

and for making O-ethyl S-phenyl ethylphosphonothioate as per the following illustrative reaction scheme:

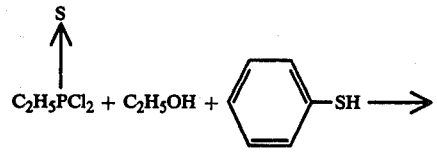

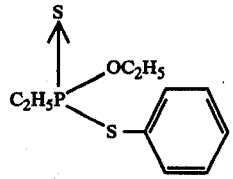

The products of the present invention are also useful as constituents in insecticides, fungicides and pharmaceuticals and as intermediates in the preparation of various other organophosphorus compounds.

The present invention will be more fully illustrated in the examples which follow.

EXAMPLE I

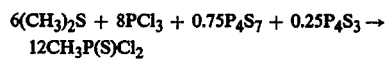

In a 300 milliliter 316 stainless steel autoclave rated at 5,000 pounds square inch gauge are placed 31 grams $(CH_3)_2S$ (0.5 mole); 91.5 grams $PCl_3$ (0.066 mole); 21.8 grams $P_4S_7$ (0.0625 mole); and 4.6 grams $P_4S_3$ (0.0209 mole). The autoclave is sealed and heated to a temperature of 330° C. This temperature is maintained for 12 hours. After cooling, the autoclave is vented and the product is removed. A 142 grams yield of crude product is obtained.

The crude product is then distilled to yield 95 grams methylphosphonothioic dichloride (64% yield). The boiling point is 36° C. at 10 mm Hg pressure ($n^{25}_D$ = 1.5470). Seventeen grams $(CH_3)_2P(S)Cl$ and 14 grams unreacted $PCl_3$ are present. The products are identified by gas-liquid chromatography and are confirmed by $^{31}$phosphorus nuclearmagnetic resonance.

EXAMPLE II

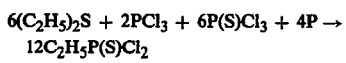

In a 30 milliliter carius tube is placed 5.4 grams $(C_2H_5)_2S$ (0.06 mole), 2.7 grams $PCl_3$ (0.02 mole), 10.1 grams $P(S)Cl_3$ (0.06 mole) and 1.2 grams yellow phosphorus (0.04 gram atoms). The tube is sealed and placed in a high pressure autoclave along with 40 milliliters $CH_2Cl_2$. The autoclave is then sealed and heated to 320° C. This temperature is maintained for 12 hours. After cooling and venting the autoclave, the Carius tube is removed and vented. The yield of crude product is 18.7 grams. Analysis of the crude product by gas-liquid chromatography gives the following results:

| Component | Weight % |
|---|---|
| $PCl_3$ | 6.6 |
| $P(S)Cl_3$ | 1.7 |
| $C_2H_5P(S)Cl_2$ | 60.5 |
| $(C_2H_5)_2P(S)Cl$ | 5.6 |
| Low boiling fraction | 13.0 |
| High boiling fraction | 12.6 |

The crude product is also analyzed by $^{31}$phosphours nuclear magnetic resonance to confirm the identity of the phosphorus compounds. In this analysis, the chemical shift relative to phosphoric acid is determined in parts per million. The results are as follows:

| Compound | Chemical Shift | Mole % Phosphorus |
|---|---|---|
| $PCl_3$ | −219.2 | 8.0 |
| $(C_2H_5)_2P(S)Cl$ | −108.8 | 6.0 |
| $C_2H_5P(S)Cl_2$ | − 94.5 | 66.0 |
| Unknowns | | 20.0 |

EXAMPLE III

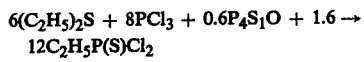

$6(C_2H_5)_2S + 8PCl_3 + 0.6P_4S_1O + 1.6 \rightarrow 12C_2H_5P(S)Cl_2$

In a 30 milliliter Carious tube is placed 5.4 grams $(C_2H_5)_2S$ (0.06 mole), 10.96 grams $PCl_3$ (0.08 mole), 2.66 grams $P_4S_1O$ (0.006 mole) and 0.49 grams yellow phosphorus (0.016 gram atoms). Using the same procedure as in Example II, the tube is heated at 340° C. for 12 hours. The yield of crude product is 18.8 grams. Analysis of the crude product by gas-liquid chromatography gives the following results:

| Compound | Weight % |
|---|---|
| $PCl_3$ | 6.8 |
| $P(S)Cl_3$ | 1.5 |
| $C_2H_5P(S)Cl_2$ | 64.1 |
| $(C_2H_5)_2P(S)Cl$ | 7.3 |
| Low boiling fraction | 7.5 |
| High boiling fraction | 12.8 |

The crude product is also analyzed by $^{31}$phosphorus nuclear magnetic resonance to confirm the identity of the phosphorus compounds. In this analysis, the chemical shift is determined as in Example II. The results are as follows:

| Compound | Chemical Shift | Mole % Phosphorus |
|---|---|---|
| $PCl_3$ | −219.1 | 7.0 |
| $(C_2H_5)_2P(S)Cl$ | −109.1 | 7.0 |
| $C_2H_5P(S)Cl_2$ | − 94.6 | 58.0 |
| Unknowns | | 28.0 |

EXAMPLE IV

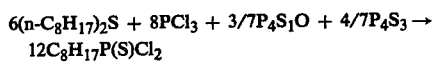

$6(n-C_8H_{17})_2S + 8PCl_3 + 3/7P_4S_1O + 4/7P_4S_3 \rightarrow 12C_8H_{17}P(S)Cl_2$ In a 3 milliliter Carious tube is placed 0.8 grams (n-$C_8H_{17})_2S$ (0.003 mole), 0.55 grams $PCl_3$ (0.004 mole), 0.095 grams $P_4S_1O$ (0.002 mole) and 0.063 grams $P_4S_3$ (0.00028 mole). Using the same procedure as in Examples II, the tube is heated at 275° C. for 12 hours. The crude product is analyzed by gas-liquid chromatography and gives the following results:

| Compound | Weight % |
|---|---|
| $PCl_3$ | 6.5 |
| $P(S)Cl_3$ | 8.0 |
| $C_8H_{17}P(S)Cl_2$ | 71.0 |
| Low boiling fraction | 14.5 |

The gas-liquid chromatography analysis shows that the product consists of four close peaks which indicates that the four possible isomers of $C_8H_{17}P(S)Cl_2$ do form.

The crude product is also analyzed by $^{31}$phosphorus nuclear magnetic resonance to confirm the identity of the phosphorus compounds.

EXAMPLE V

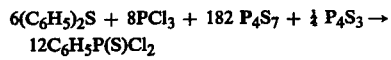

$6(C_6H_5)_2S + 8PCl_3 + 182 P_4S_7 + \frac{1}{4} P_4S_3 \rightarrow 12C_6H_5P(S)Cl_2$ In a 30 milliliter Carius tube is placed 5.58 grams $(C_6H_5)_2S$ (0.03 mole); 5.48grams $PCl_3$ (0.04 mole); 1.3 grams $P_4S_7$ (0.00375 mole); and 0.275 grams $P_4S_3$ (0.00125 mole). Using the same procedure as in Example II, the tube is heated at 330° C. for 12 hours. The autoclave is cooled to 70° C. and opened and allowed to cool to room temperature.

The yield of crude product, a dark liquid, is 12.2 grams. This product is distilled under vacuum to give 4.5 grams phenylphosphonothioic dichloride, a 36 percent yield. The boiling point at 1 mm Hg is 77°–83° C. and $n_D{}^{25} = 1.6239$ (reference $C_6H_5P(S)Cl_2$ $n_D{}^{25} = 1.6245$).

The product is also analyzed by $^{31}$phosphorus nuclear magnetic resonance to confirm its identity.

Having set forth the general nature and some examples of the present invention, the scope is now particularly set forth in the appended claims.

What is claimed is:

1. A method of preparing compounds of the formula:

(I)

wherein R is selected from the group consisting of $C_1$ to $C_{20}$ alkyl; the aryl substituted derivatives thereof; said aryl having 1 or 2 fused rings, cycloalkyl of 5–6 carbons in the ring; aryl of up to 3 fused rings; biphenyl and the $C_1$–$C_4$ alkyl substituted derivatives of said cycloalkyl, aryl and biphenyl and X is chlorine or bromine, comprising contacting under at least an autogenous pressure at a temperature of from about 200° C. to about 400° C. a dialkyl or diaryl thioether reactant of the formula: wherein R is as defined above, with phosphorus and halogen containing reactants selected from the group consisting of $PX_3$ and $P(S)X_3$, where X is as defined above; and with reactants selected from the group consisting of $P_4S_3$, $P_4S_5$, $P_4S_7$ and $P_4S_{10}$; and additionally, elemental phosphorus.

2. The method of claim 1 wherein R is alkyl including methyl, ethyl, n-propyl, isopropyl, n-butyl, isobutyl, tert-butyl, pentyl, hexyl, heptyl, octyl, nonyl, decyl, dodecyl, tetradecyl, hexadecyl, octadecyl and eicosyl.

3. The method of claim 1 wherein R is aralkyl including phenymethyl, phenylethyl, phenylbutyl, phenyloctyl, phenylhexadecyl, and the corresponding naphthyl derivatives.

4. The method of claim 1 wherein R is cycolalkyl including cyclopentyl and cyclohexyl.

5. The method of claim 1 wherein R is aryl including phenyl, methylphenyl, ethylphenyl, propyphenyl, and butylphenyl, naphthyl, methylnaphthyl, ethylnaphthyl, propylnaphthyl, butylnaphthyl, anthryl, methylanthryl, propylanthryl, butylanthryl, as well as dimethylphenyl, dimethylnaphthyl, diethylanthryl and, biphenyl.

6. The method of claim 1 wherein the reactants are contacted approximately according to the following general elemental scheme:

$$R_2S + 2P + S + 2X_2 \rightarrow 2RP(S)X_2 \qquad (2)$$

where R and X are as defined in claim 1.

UNITED STATES PATENT AND TRADEMARK OFFICE
CERTIFICATE OF CORRECTION

PATENT NO. : 4,130,583
DATED : December 19, 1978
INVENTOR(S) : Eugene H. Uhing et al.

It is certified that error appears in the above–identified patent and that said Letters Patent are hereby corrected as shown below:

In the Abstract, line 4, "$P_4S_1O$" should read -- $P_4S_{10}$ --.

Column 3, line 9, after "quantity of", please insert -- phosphorus and sulfur --.

Column 3, line 33, "sight" should read -- slight --.

Column 6, line 41, after "pounds" please insert -- per --.

Column 6, line 48, "grams" should be -- gram --.

Column 7, line 13, "phosphours" should be -- phosphorus --.

Column 7, line 32, "$P_4S_1O$" should be -- $P_4S_{10}$ --.

Column 7, line 61, "$P_4S_1O$" should be -- $P_4S_{10}$ --.

Column 7, line 66, "$P_4S_1O$" should be -- $P_4S_{10}$ --.

UNITED STATES PATENT AND TRADEMARK OFFICE
CERTIFICATE OF CORRECTION

PATENT NO. : 4,130,583
DATED : December 19, 1978
INVENTOR(S) : Eugene H. Uhing et al.

It is certified that error appears in the above-identified patent and that said Letters Patent are hereby corrected as shown below:

Column 8, line 18, "182 $P_4S_7$" should be -- 3/4 $P_4S_7$ --.

Column 8, line 51, "$C_2O$" should be -- $C_{20}$ --.

Column 8, line 58, after "formula:" please insert -- $R_2S$ --.

Column 9, line 2, "phenymethyl" should be -- phenylmethyl --.

Signed and Sealed this

Twenty-fourth Day of April 1979

[SEAL]

Attest:

RUTH C. MASON
Attesting Officer

DONALD W. BANNER
Commissioner of Patents and Trademarks